United States Patent [19]

Rapoport et al.

[11] 4,159,993
[45] Jul. 3, 1979

[54] 3-METALLO SUBSTITUTED NAPHTHALENES

[75] Inventors: Henry Rapoport, Berkeley; Clinton D. Snyder, Monte Sereno, both of Calif.

[73] Assignee: The Regents of the University of California, Berkeley, Calif.

[21] Appl. No.: 815,771

[22] Filed: Jul. 14, 1977

Related U.S. Application Data

[60] Division of Ser. No. 565,473, Apr. 7, 1975, Pat. No. 4,089,873, which is a continuation-in-part of Ser. No. 540,450, Jan. 13, 1975, abandoned.

[51] Int. Cl.$^2$ .............................................. C07F 1/08
[52] U.S. Cl. .............................. 260/438.1; 260/396 K
[58] Field of Search ...................................... 260/438.1

[56] References Cited

U.S. PATENT DOCUMENTS 3,658,863  4/1972  Harrison ........................... 260/438.1
3,798,248  3/1974  van Koten et al. ............... 260/438.1

OTHER PUBLICATIONS

Coates et al., Organometallic Compounds, Methuen & Co. Ltd., London, vol. 2, 3rd Ed., pp. 253-254 (1968).
Chemical Abstracts, 31 1015.
Chemical Abstracts, 71 50163s (1969).
Camus et al., J. Organometallic Chem. 14, p. 441 (1968).

*Primary Examiner*—Helen M. S. Sneed
*Attorney, Agent, or Firm*—Bernard & Brown

[57] ABSTRACT

3-Prenyl-substituted menaquinones are made by reacting a 3-metallo-2-alkyl-1,4-di(alkoxy or aralkoxy) naphthalene with a prenyl halide, and then oxidizing the resulting 3-prenyl-2-alkyl-1,4-di(alkoxy or aralkoxy) naphthalene to prepare the corresponding 3-prenyl-substituted menaquinone. The metallo substituent at the 3-position may be Li, Li/Cu, Cu or MgBr. The oxidation is advantageously conducted by the use of argentic oxide.

12 Claims, No Drawings

3-METALLO SUBSTITUTED NAPHTHALENES

This is a division of application Ser. No. 565,473, filed Apr. 7, 1975, now U.S. Pat. No. 4,089,873, which is in turn a continuation-in-part of Ser. No. 540,450, filed Jan. 13, 1975, now abandoned.

This invention relates to a method of synthesizing menaquinones, and particularly 3-prenyl-2-alkyl menaquinones. The invention includes the preparation of 3-metallo-2-alkyl-1,4-di(alkoxy or aralkoxy) naphthalenes, and these intermediates have as the 3-metallo substituent lithium, lithium/copper copper or magnesium bromide. The invention provides as novel compounds the intermediates in which the 3-metallo substituent is lithium/copper, copper or magnesium bromide. According to the invention the 3-metallo intermediates can be reacted with a prenyl halide to prepare the corresponding 3-prenyl-2-alkyl-1,4-di(alkoxy or aralkoxy) naphthalenes, which can be oxidized to the corresponding 3-prenyl-2-alkyl menaquinones. It is a further aspect of the invention that the oxidation is advantageously conducted by the use of argentic oxide.

The 3-prenyl-2-alkyl menaquinones prepared by this invention have the structural formula:

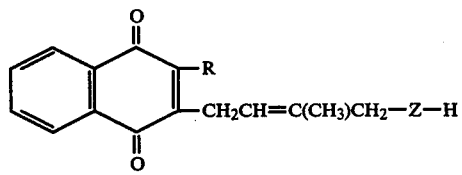

wherein R is alkyl, for instance, lower alkyl, say of 1 to about 4 or 8 atoms, preferably methyl, and wherein Z is $-\{CH_2CH=C(CH_3)CH_2\}_m$, $-\{CH_2CH_2CH(CH_3)CH_2\}_n$ or combinations thereof, and in which each of m and n, and their sum may be 0 to about 25 or more, and frequently, each of m and n and their sum are 0 to 1 to about 9 or 12. For convenience, these compounds are sometimes hereafter referred to as the MK Compounds or the MK-integer Compounds wherein the integer represents the value of m plus n plus 1. These compounds have heretofore been designated as being in the vitamin K series, see U.S. Pat. No. 2,348,037, and can be administered to red-blooded animals in the usual manner as vitamin K compounds to combat bleeding. The MK Compounds wherein the prenyl component at the 3-position carbon has the trans configuration exhibit the greatest anti-hemorrhagic activity, especially when R is methyl. By the method of this invention, the MK Compounds can be prepared without undue degradation of the prenyl substituent or reactant, and the stereoconfiguration at the olefinic bond in the prenyl halide reactant or prenyl substituent can be maintained.

There have been numerous attempts to prepare prenyl-substituted menaquinones, but difficulties have been encountered in terms of undesirably low yields, maintenance of the stereoconfiguration of the prenyl structure, instability of the prenyl reactant in the case of using it as an allylic alcohol, and side reactions such as side chain isomerization or chromal cyclization. For example, an approach to the synthesis of MK Compounds which has been suggested involved the condensation of 2-methyl-1,4-naphthoquinol with an allylic alcohol in the presence of an acidic catalyst such as boron trifluoride etherate. The resulting menaquinol can be converted by mild oxidation to the corresponding menaquinone. This suggested route for synthesizing the MK Compounds has not, however, proven to be entirely satisfactory in that under the acidic conditions employed for alkylation, the allylic alcohol is unstable, and thus the yields of MK Compounds based on the allylic alcohol reactant are low. Another approach which has been suggested is through the use of N-sulfinylamine ester of the prenyl component as the reactant to prepare MK Compounds from, for instance, 2-methyl-1,4-naphthoquinol. This reaction, however, proceeds with poor yields of MK Compounds.

By the present invention it has been found that 3-prenyl-2-alkyl menaquinones can be made without encountering to undesirable extents the difficulties previously experienced in such syntheses as noted above. In the new procedure the naphthalenic compound is activated at the 3-position carbon with a metallo-substituent and then reacted with an appropriately functionalized prenyl halide component to prepare MK Comounds. The reaction need not be conducted in the presence of the acidic or other conditions which degradate or isomerize the prenyl component or under conditions which unduly detract from selective prenylation at the 3-position carbon of the naphthalene component. Thus, in accordance with this invention, a 2-alkyl-1,4-di(alkoxy or aralkoxy) naphthalene is activated at the 3-position carbon in the form of corresponding 3-metallo-substituted naphthalene of the formula:

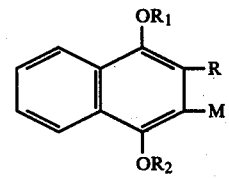

wherein R is as defined above, $R_1$ and $R_2$ may be the same or different hydrocarbyl groups and may be alkyl, say lower alkyl of, for instance, 1 to about 4 or 8 carbon atoms, or aralkyl. The aralkyl groups may have, for example, 7 to about 10 or 12 carbon atoms, e.g. benzyl, phenethyl or other monocyclic groups. Conveniently $R_1$ and $R_2$ are methyl. M is a metal-containing substituent such as —Li, —(CuLi)$_{\frac{1}{2}}$, —MgBr, —Cu and the like.

In the invention, the 3-metallo naphthalene is reacted with a prenyl-type component of the formula

$$X-CH_2CH=C(CH_3)CH_2-Z-H$$

wherein X is halogen, preferably having an atomic number from 17 to 35, i.e., chlorine or bromine, and most preferably bromine, and wherein Z is as defined above, e.g. to provide a prenyl, geranyl, solanesyl, phytyl or like group. The prenyl component is preferably of trans configuration to a major extent and most preferably is substantially entirely of this structure. The prenyl alkylation reaction yields compounds of the formula

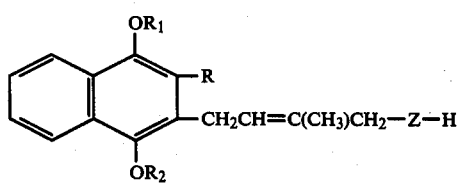

wherein R, $R_1R_2$ and Z are as defined above. These products can be oxidized to the corresponding prenyl-substituted menaquinones. This method of synthesizing the prenyl-substituted menaquinones provides these products in high yields and with the maintenance of the stereoconfiguration of the prenyl reactant to a great extent and the prenyl substituent may be substantially entirely of the same configuration as in the prenyl halide reactant.

The prenyl alkylation reaction proceeds at room temperature. The temperature employed during this reaction may be lower or higher than ambient temperature, but generally may be about 5 or 10° C. to about 50° or 60° C., preferably about 15° C. to 35° C. The reaction is preferably conducted under non-acidic conditions and can be performed in an inert atmosphere which conveniently may be nitrogen, and may be conducted in the presence of an inert solvent, for instance, diethyl ether or petroleum ether, and under non-acidic conditions.

The prenylated naphthalenes which are obtained in accordance with method of this invention have protected oxygen functions at the 1 and 4-carbon positions of the naphthalene nucleus. Keto functions at the 1 and 4-positions, i.e., the corresponding menaquinones, can be obtained without undue adverse effect on the prenyl substituent, by subjecting the prenylated naphthalene to oxidation. The oxidation is preferably effected by, for instance, using silver (II) oxide (argentic oxide) as an oxidizing reagent and this reaction can be conducted in the presence of an acid; although the oxidation may be done in other ways, e.g. by bubbling oxygen through a solution of the prenylated naphthalene or by treatment of the prenylated naphthalene with ferric ion. Generally, the reaction can be conducted under relatively mild oxidation conditions.

The 3-metallo naphthalenes which may be employed in connection with this invention to provide the MK Compounds can be prepared from the corresponding 3-bromo-2-alkyl-1,4-disubstituted naphthalenes. The 3-bromo-2-alkyl-1,4-disubstituted naphthalene can be treated with butyllithium in, for instance, the manner described by Snyder et al. in *J. Org. Chem.*, 36, 3451 (1971), herein incorporated by reference, to prepare the corresponding 3-metallo naphthalene wherein M is lithium, i.e., 3-lithio-2-alkyl-1,4-disubstituted naphthalene. The reaction between the 3-bromo-2alkyl-1,4-disubstituted naphthalene and butyllithium proceeds at room temperature. An inert organic solvent such as diethyl ether or petroleum ether may be employed in the reaction. The solvent may be used in quantities suitable for dissolving the organic reactants, for instance, in weight ratio to the bromo-substituted naphthalene reactant of about 1:1 to 500:1 or more.

The 3-lithio-2-alkyl-1,4-disubstituted naphthalene compounds can be converted to the compounds wherein M is $(CuLi)_{\frac{1}{2}}$ by adding cuprous halide such as a bromide or chloride, preferably cuprous bromide, to the 3-lithio-naphthalene compound. The cuprous halide is frequently provided in an amount of about 0.3 to 0.7, preferably about 0.4 to 0.6, mole of cuprous ion per mole of the 3-lithio-naphthalene compound. The reaction to prepare 3-lithio-2-alkyl-1,4-disubstituted naphthyl cuprate is conveniently conducted at room temperature, i.e., about 15° to 35° C., under agitation. The time of the reaction is brief, for instance, good conversion may be obtained in about 0.5 to 50 minutes. The reaction may be conducted in the presence of an inert solvent, for instance, dry tetrahydrofuran. The solvent may be used in quantities suitable for dissolving the organic reactants, for instance, in a weight ratio of solvent to the naphthalene derivative reactant of about 1:1 to 500:1 or more.

The 3-bromo-2-alkyl-1,4-disubstituted naphthalenes may alternatively be converted to the corresponding Grignard reagent, that is, where M is magnesium bromide. The conversion may be effected by adding magnesium metal to the 3-bromo-2-alkyl-1,4-disubstituted naphthalene. Preferably, the magnesium metal used is freshly prepared in finely divided form, for instance, as fresh magnesium filings. Frequently, the molar ratio of magnesium metal to the 3bromo reactant is about 0.9 to 2, preferably about 0.95 to 1.2. The reaction proceeds at room temperature; however, elevated or reduced temperatures may be employed, for instance, from about 5° to 50° C., preferably about 10° to 35° C. The reaction can be conducted in an inert solvent such as diethyl ether or petroleum ether. The solvent may be used in quantities suitable for dissolving the organic reactants, for instance, in a weight ratio of solvent to the naphthalene derivative reactant of about 1:1 to 500:1, or more.

The Grignard reagent, 2-alkyl-1,4-disubstituted-naphthyl-3-magnesium bromide, can be treated with a cuprous halide, such as a bromide or chloride, preferably cuprous bromide, to prepare the corresponding compounds wherein M is copper, i.e., a 3-cupro-2-alkyl-1,4-disubstituted naphthalene. The cuprous halide is conveniently provided in a molar ratio to the Grignard reagent of about 0.9:1 to 2:1, preferably about 0.95:1 to 1.2:1. The reaction proceeds at room temperature, but higher or lower reaction temperatures may be employed, for instance, from about 5° to 50° C., preferably about 10° to 35° C. The reaction may be conducted in an inert solvent such as diethyl ether or petroleum ether, in quantities suitable for dissolving the organic reactants, for instance, in a weight ratio of solvent to the naphthalene derivative reactant of about 1:1 to 500:1.

The 3-metallo-2-alkyl-1,4-disubstituted naphthalenes are reacted with a prenyl-type compound, e.g. a prenyl halide such as a chloride or bromide, to achieve prenylation and obtain the 1,4-diether of the MK Compounds. A prenyl-type halide may be obtained from the corresponding prenyl alcohol by conventional procedures such as that disclosed by Isler, et al., *Helv. Chem. Acta*, Volume 39, page 897 (1956), herein incorporated by reference. The corresponding alcohols are frequently more readily available than the prenyl halides. Commonly available prenyl alcohols include trans-geraniol, cis-nerol, farnesol, phytol, and solanesol. The prenyl-type compound may be substituted with one or more hydrocarbyl-containing groups in place of a hydrogen bonded to a carbon atom. The hydrocarbyl-containing group may be, for instance, alkyl of from 1 to about 30 carbon atoms.

Since often the prenyl-type halide is the more valuable of the starting materials, the 3-metallo-2-alkyl-1,4-disubstituted naphthalene may desirably be employed in stochiometric or in excess of stoichiometric amounts. For instance, the molar ratio of prenyl halide to 3-metallo naphthalene derivative reactant may be about 0.5:1 to 2:1, preferably about 0.95:1 to 1.5:1. The reaction may proceed rapidly, and frequently the duration of the reaction is about 0.1 to 20 hours.

The product of the reaction involving the prenyl-type halide and 3-metallo-2-alkyl-1,4-disubstituted naphthalene is a correspondng 1,4-diether naphthalene which can be converted to the MK Compounds by oxidation. By one method, the oxidation may be carried out using a reaction mixture containing silver (II) oxide as an oxygen source, and a strong acid. The acid is preferably a mineral acid such as nitric acid, sulfuric acid, or hydrochloric acid. The reaction proceeds quickly at room temperature, often in less than about 2 hours, and reaction temperatures of about 5° to 50° C., preferably about 15° to 35° C., are employed.

The silver (II) oxide may be provided in the reaction mixture in a molar ratio (calculated as AgO) to the diether naphthalene reactant of about 1:1 to 5:1, preferably about 2:1 to 3:1, and high conversions to MK-2Compound wherein R is methyl have been observed using a ratio of about 2.2:1. Lesser amounts of oxidizing agent could be employed; however, it is often commercially advantageous to supply the silver (II) oxide in stoichiometric excess. The acid can be provided in a molar amount of about 1 to 5, preferably about 2 to 4, times the amount of diether naphthalene reactant. The oxidation is preferably conducted in the presence of a solvent such as dioxane. The solvent may be provided in an amount suitable for dissolving the organic reactants, e.g. about 5 to 1000, preferably about 50 to 500, times the weight amount of diether naphthalene. In addition to the water which may be supplied with the acid, water may be used with the solvent, for instance, in a volume ratio of about 0.01:1 to 1:1 to the solvent.

The recovery of the MK Compounds may be effected by conventional means, for instance, by extraction with petroleum ether and water or aqueous salt solution. Column chromatography using, for instance, kieselgel absorbent, is also useful.

The MK Compounds may be substituted at one or more of the 5,6,7 and 8 position with, for instance, lower alkyl or lower alkoxy having 1 to about 8 carbon atoms. Such substituted MK Compounds may be prepared employing a corresponding, substituted naphthoquinol or naphthoquinone as the starting material where the substituent is non-reactive during the synthesis of the MK compound, or the substituent may be appropriately blocked during the reaction and later recovered to obtain the desired, substituted MK Compound.

In the following examples which illustrate the invention, the reactions are conducted at room temperature and under a nitrogen atmosphere unless otherwise indicated, and all parts and percentages are by weight unless otherwise noted.

EXAMPLE 1

3.31 Grams of tri-n-butylphosphine is added dropwise to a solution of 1.54 grams of trans-geraniol (99 percent) in 20 milliliters of carbon tetrachloride which has been distilled from $P_2O_5$. The reaction mixture is then diluted with petroleum ether and the solvent is decanted from the residual viscous tri-n-butylphosphine oxide. After the solvent is removed, the residue is purified by distillation at 70° C. and 1 millimeter pressure to yield essentially pure trans-geranyl chloride.

EXAMPLE 2

About 281 milligrams of 3-bromo-2-methyl-1,4-dimethyloxynaphthalene (1.0 millimole) is dissolved in two milliliters of petroleum ether and a mixture of about 64 milligrams of butyllithium (1.0 millimole) in 0.62 milliliters of hexane is added thereto. A white precipitate results and water is added. 3-Lithio-2-methyl-1,4-dimethpoxynaphthalene is in the ether layer and is recovered.

EXAMPLE 3

About 104 milligrams of 3-lithio-2-methyl-1,4-dimethoxynaphthalene (0.5 millimole) prepared as in Example 2, is quenched with 0.5 milliliter of deuteium oxide, and the crude product is obtained by extraction with petroleum ether. Nmr integration of the 3-aromatic proton versus the 5,6,7,8-protons indicated 99 percent deuterium at the 3-position.

EXAMPLE 4

Approximately 36 milligrams of cuprous bromide (0.25 millimole) are added to about 104 milligrams of 3-lithio-2-methyl-1,4-dimethoxynaphthalene (0.5 millimole) prepared as in Example 2, in a petroleum ether solvent. The reaction mixture is subjected to vigorous stirring for about 15 minutes and a brownish precipitate forms in the reaction mixture. The brownish precipitate is lithium 3-(2-methyl-1,4-dimethoxy) dinaphthyl cuprate.

EXAMPLE 5

About 12 milligrams of freshly prepared magnesium filings (0.5 millimole) are added to about 141 milligrams of 3-bromo-2-methyl-1,4-dimethoxynaphthalene (0.5 millimole) in 1 milliliter of dry tetrahydrofuran. The mixture is stirred for 3 hours at room temperature. The resulting clear solution contains 2-methyl-1,4-dimethoxynaphthalene-3-magnesium bromide.

EXAMPLE 6

2-Methyl-1,4-dimethoxynaphthalene-3-magnesium bromide is quenched with deuterium oxide, and 2-methyl-1,4-dimethoxynaphthalene is obtained by extraction with petroleum ether. Nmr integration of the 3-aromatic proton versus the 5,6,7,8-protons indicated 97 percent deuterium at the 3-position.

EXAMPLE 7

About 153 milligrams of 2-methyl-1,4-dimethoxynaphthalene-3-magnesium bromide (0.5 millimole) are mixed with 72 milligrams of cuprous bromide (0.5 millimole) in a tetrahydrofuran solvent and after a brief stirring of the reaction mixture, a gelatinous precipitate is formed which upon further stirring provides a homogeneous clear solution of 3-cupro-2-methyl-1,4-dimethoxynaphthalene in tetrahydrofuran.

EXAMPLE 8

About 86 milligrams of trans-geranyl chloride (0.5 millimole) prepared as in Example 1 are added to about 208 milligrams of 3-lithio-2-methyl-1,4-dimethoxynaphthalene (0.5 millimole) in a reaction vessel. The reaction vessel is sealed in vacuo. The reaction mixture is heated at 50° C. for 68 hours after which the vessel is opened and the geranyl chloride which is unreacted is determined to be 80 percent by gas chromatography. The reaction mixture is diluted with petroleum ether, the salts are removed by centrifugation, and crude product is obtained by evaporation of solvents. Column chromatography using Camag kieselgel absorbent gave 17 milligrams of the dimethyl ether of MK-2 Compound wherein R is methyl and 62 milligrams of 2-methyl-1,4-dimethoxynaphthalene.

EXAMPLE 9

A mixture of 108 milligrams of trans-geranyl bromide (0.5 millimole) and about 236 milligrams of lithium 3-(2-methyl-1,4-dimethoxy)dinaphthalene cuprate (0.5 millimole) is added to a reaction vessel. The reaction vessel is sealed as in Example 8 and after stirring for 17 hours the reaction mixture is partitioned between petroleum ether and water. Upon evaporation of the organic solvent a crude product is obtained which is chromatographed using essentially the same procedure described in Example 8 to yield 125 milligrams of the dimethyl ether of MK-2 Compound wherein R is methyl.

EXAMPLE 10

About 108 milligrams of trans-geranyl bromide (0.5 millimole) is added to about 168 milligrams of 2-methyl-1,4-dimethoxynaphthalene-3-magnesium bromide (0.55 millimole) in a 1.1 molar solution of tetrahydrofuran. The reaction is conducted in essentially the same manner as described in Example 9 and after 17 hours the reaction mixture is diluted with petroleum ether. The salts are removed by centrifugation and the solvents are evaporated to provide a crude product which is chromatographed to yield a mixture of 156 milligrams of the dimethyl ether of MK-2 Compound wherein R is methyl and minor amounts of 3-bromo-2-methyl-1,4-dimethoxynaphthalene and 2-methyl-1,4-dimethoxynaphthalene. The dimethyl ether of MK-Compound is not separated from the 3-bromo-2-methyl-1,4-dimethoxynaphthalene.

EXAMPLE 11

To 84.5 milligrams of the product mixture provided by Example 10 (about 0.254 millimole of total dimethoxy naphthalene compounds) is added 68.2 milligrams silver (II) oxide (0.55 millimole), 2.5 milliliters of dioxane and 0.25 milliliters of water. 92 Microliters of 6.2N nitric acid are added to the mixture to accomplish the oxidation. The reaction mixture is then partitioned between 19 milliliters of petroleum ether and 2 milliliters of water. The organic phase is extracted twice with 3 milliliters of water and then is evaporated to provide a residue. The residue is column chromatographed to provide 60 milligrams of trans-MK-2 Compound wherein R is methyl.

EXAMPLE 12

The procedures of Examples 10 and 11 are essentially repeated except employing cis-neryl bromide instead of transgeranyl bromide. In the oxidation, 34 milligrams of the dimethyl ether of MK-2 Compound and 3-bromo-2-methyl-1,4-dimethoxynaphthalene (about 0.1 millimole of total dimethoxy naphthalene compounds); 27 milligrams of silver (II) oxide (0.22 millimole); 1 milliliter of dioxane; 0.1 milliliter of water; and 38 microliters of 6.2N nitric acid are employed. About 24 milligrams of cis-MK-2 Compound wherein R is methyl are obtained (85 percent cis).

EXAMPLE 13

About 108 milligrams of trans-geranyl bromide (0.5 millimole) is added to about 132 milligrams of 3-cupro-2-methyl-1,4-dimethoxynaphthalene (0.5 millimole) and an immediate precipitation of cuprous bromide occurs. The reaction mixture is stirred for one hour and then diluted with petroleum ether and the product is isolated as in Example 10 to provide a mixture of 138 milligrams of the dimethyl ether of MK-2 Compound wherein R is methyl and 10 milligrams of 3-bromo-2-methyl-1,4-dimethoxynaphthalene.

This mixture is oxidized using essentially the same procedure described in Example 11 except using 2.5 mole equivalents of silver (II) oxide and 2.6 mole equivalents of nitric acid to provide trans-MK-2 Compound wherein R is methyl (97 percent trans.)

EXAMPLE 14

Essentially the same procedure is followed as set forth in Example 10 except that 3-lithio-2-methyl-1,4-dimethoxynaphthalene is employed instead of 2-methyl-1,4-dimethoxynaphthalene-3-magnesium bromide. The dimethyl ether of MK-2 Compound wherein R is methyl is prepared.

EXAMPLE 15

Essentially the same procedure is followed in this example as used in Example 10 except that trans-geranyl chloride is employed instead of trans-geranyl bromide. The dimethyl ether of MK-2 Compound wherein R is methyl is prepared.

EXAMPLE 16

A mixture of about 113 milligrams of 2-methyl-1,4-dimethoxynaphthalene-3-magnesium bromide (0.37 millimole) and 208 milligrams trans-solanesyl bromide (0.3 millimole) is prepared. The reaction mixture is permitted to stand for 18 hours and petroleum ether is then added to the mixture. The precipitate of salts is removed and the residue obtained by solvent evaporation is resolved by column chromatography using Camag kieselgel absorbent to provide 232 milligrams of the dimethyl ether of MK-9 Compound.

The dimethyl ether of MK-9 Compond in an amount of 163 milligrams (about 0.2 millimole total dimethoxynaphthalene) is mixed with 62 milligrams of silver (II) oxide in 3 milliliters of dioxane and 0.2 milliliter of water. 84 Microliters of 6.2N nitric acid are added to the mixture, and the reaction mixture is stirred until a complete solution is obtained. The reaction mixture is then partitioned between 10 milliliters of petroleum ether and 2 milliliters of water. The organic phase is washed twice with 3 milliliters of water and the solvent is evaporated. The residue is resolved by column chromatography to yield 110 milligrams of MK-9 (98 percent $\Delta^2$-trans). The residue also contains 35 milligrams of the starting material.

When the oxidation reaction is repeated using 3.0 molar equivalents of silver (II) oxide and 3.1 molar equivalents of nitric acid, essentially complete consumption of the dimethyl ether of MK-9 wherein R is methyl occurs.

EXAMPLE 17

2-Methyl-3-bromomagnesio-1,4-dimethoxynaphthalene (0.55 mmol, 1.1M) is prepared as in Example 5, and phytyl bromide (0.50 mmol) is added thereto. After 17 hours the reaction mixture is diluted with petroleum ether, the salts are removed by centrifugation, and the solvents evaporated to give the crude product which is chromatographed on silica to give 2-methyl-3-trans-phytyl-1,4-dimethoxynaphthalene. This dimethyl ether (0.25 mmol) and argentic oxide (0.55 mmol) are mixed, and dioxane (2.5 ml) and water (0.25 ml) are added. Addition of nitric acid (6.2N, 92 microliters, 0.57 mmol) accomplishes the oxidation. The reaction mixture is then partitioned between petroleum ether (19 ml) and water (2ml), and the organic phase is extracted twice with water using 3 ml each time, and then evaporated. Chromatography of the residue gives an 87% yield of trans-phylloquinone.

It is claimed:

1. Compounds of the formula

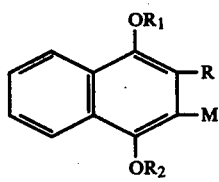

wherein R is lower alkyl and $R_1$ and $R_2$ are lower alkyl, or aralkyl of 7 to about 12 carbon atoms, and M is selected from the group consisting of $(CuLi)_{\frac{1}{2}}$ and Cu.

2. The compounds of claim 1 wherein R is methyl.

3. The compounds of claim 2 wherein $R_1$ and $R_2$ are methyl.

4. A method of preparing lithium-3-naphthyl cuprate of the formula

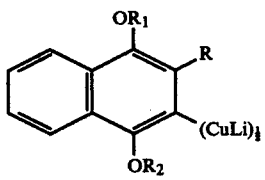

wherein R is lower alkyl, $R_1$ and $R_2$ are lower alkyl, or aralkyl of 7 to about 12 carbon atoms, comprising reacting cuprous halide with 3-lithio-naphthalene of the formula

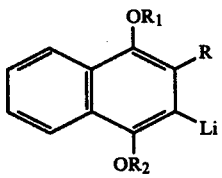

in a molar ratio of cuprous halide to 3-lithio-naphthalene of from about 0.3 to 0.7 to prepare the lithium-3-naphthalene cuprate.

5. The method of claim 4 wherein the cuprous halide is cuprous bromide.

6. The method of claim 5 wherein the reaction is conducted with about 0.4 to 0.6 mole of cuprous bromide per mole of the 3-lithio-naphthalene.

7. The method of claim 5 wherein R, $R_1$ and $R_2$ are methyl.

8. A method of preparing 3-cupro-naphthalene of the formula

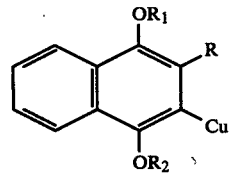

wherein R is lower alkyl, $R_1$ and $R_2$ are lower alkyl, or aralkyl of 7 to about 12 carbons, comprising reacting naphthyl-3-magnesium bromide of the formula with cuprous halide in a molar ratio of from about 0.9 to 2 moles of cuprous halide per mole of naphthyl-3-magnesium bromide to prepare the 3-cupro-naphthalene.

9. The method of claim 8 wherein R, $R_1$ and $R_2$ are methyl.

10. The method of claim 9 wherein the reaction is conducted with about 0.95 to 1.2 moles of cuprous halide per mole of naphthyl-3-magnesium bromide.

11. The method of claim 10 in which the cuprous halide is cuprous bromide.

12. The method of claim 11 wherein the reaction is conducted in the presence of tetrahydrofuran solvent.

* * * * *

UNITED STATES PATENT OFFICE
CERTIFICATE OF CORRECTION

Patent No. 4,159,993          Dated July 3, 1979

Inventor(s) Henry Rapoport and Clinton D. Snyder

It is certified that error appears in the above-identified patent and that said Letters Patent are hereby corrected as shown below:

Column 1, line 13, after "lithium/copper" insert --,--.

Column 1, line 35, after "4 or 8" insert --carbon--.

Column 1, line 39, delete the first occurrence of the word "to" and substitute therefor --or--.

Column 2, line 17, delete "compound" and substitute therefor --component--.

Column 4, line 14, after "3" insert a hyphen.

Column 5, line 14, after "2" insert a space.

Column 5, lines 58 and 61 should be flush with the left margin.

Column 6, line 1, delete "dimethpoxynaphthalene" and substitute therefor --dimethoxynaphthalene--.

UNITED STATES PATENT OFFICE
CERTIFICATE OF CORRECTION

Patent No. 4,159,993      Dated July 3, 1979

Inventor(s) Henry Rapoport and Clinton D. Snyder

It is certified that error appears in the above-identified patent and that said Letters Patent are hereby corrected as shown below:

Column 6, line 58 the words "in vacuo" should be in italics.

Throughout the patent application the words "trans" and "cis" are underlined, but are not underlined or italicized in the patent deed.

Signed and Sealed this

First Day of January 1980

[SEAL]

Attest:

SIDNEY A. DIAMOND

Attesting Officer     Commissioner of Patents and Trademarks